(12) United States Patent
Lim

(10) Patent No.: US 9,717,625 B2
(45) Date of Patent: Aug. 1, 2017

(54) INTRAVASCULAR HEAT EXCHANGE CATHETER WITH NON-ROUND COILED COOLANT PATH

(71) Applicant: Zoll Circulation, Inc., Sunnyvale, CA (US)

(72) Inventor: Alex L. Lim, Santa Clara, CA (US)

(73) Assignee: Zoll Circulation, Inc., Sunnyvale, CA (US)

( * ) Notice: Subject to any disclaimer, the term of this patent is extended or adjusted under 35 U.S.C. 154(b) by 857 days.

(21) Appl. No.: 13/653,565

(22) Filed: Oct. 17, 2012

(65) Prior Publication Data

US 2014/0094882 A1 Apr. 3, 2014

Related U.S. Application Data

(60) Provisional application No. 61/707,130, filed on Sep. 28, 2012.

(51) Int. Cl.
*A61F 7/12* (2006.01)

(52) U.S. Cl.
CPC .......... *A61F 7/12* (2013.01); *A61F 2007/126* (2013.01)

(58) Field of Classification Search
CPC .............................. A61F 7/12; A61F 2007/126
USPC .......................... 607/104, 105, 106; 606/192
See application file for complete search history.

(56) References Cited

U.S. PATENT DOCUMENTS

| | | |
|---|---|---|
| 1,459,112 A | 6/1923 | Mehl |
| 1,857,031 A | 5/1932 | Schaffer |
| 2,663,030 A | 12/1953 | Dahlberg |
| 2,673,987 A | 4/1954 | Upshaw et al. |
| 3,225,191 A | 12/1965 | Calhoun |
| 3,369,549 A | 2/1968 | Armao |
| 3,425,419 A | 2/1969 | Actis Dato |
| 3,504,674 A | 4/1970 | Swenson |
| 3,726,269 A | 4/1973 | Webster, Jr. |
| 3,744,555 A | 7/1973 | Fletcher et al. |
| 3,751,077 A | 8/1973 | Hiszpanski |
| 3,937,224 A | 2/1976 | Uecker |
| 3,945,063 A | 3/1976 | Matsuura |
| 4,038,519 A | 7/1977 | Foucras |
| 4,065,264 A | 12/1977 | Lewin |
| 4,103,511 A | 8/1978 | Kress et al. |
| 4,126,132 A | 11/1978 | Portner et al. |
| 4,153,048 A | 5/1979 | Magrini |
| 4,173,228 A | 11/1979 | Van Steenwyk et al. |
| 4,181,132 A | 1/1980 | Parks |
| 4,298,006 A | 11/1981 | Parks |
| 4,459,468 A | 7/1984 | Bailey |
| 4,532,414 A | 7/1985 | Shah et al. |
| 4,554,793 A | 11/1985 | Harding, Jr. |
| 4,581,017 A | 4/1986 | Sahota |

(Continued)

FOREIGN PATENT DOCUMENTS

| | | |
|---|---|---|
| DE | 19531935 | 2/1997 |
| GB | 2040169 | 8/1980 |

(Continued)

OTHER PUBLICATIONS

F.W. Behmann, E. Bontke, "Die Regelung der Wärmebildung bei künstlicher Hypothermie", Pflügers Archiv, Bd. 266, S. 408-421 (1958).

(Continued)

*Primary Examiner* — Joseph Stoklosa
*Assistant Examiner* — Yasamin Ekrami
(74) *Attorney, Agent, or Firm* — John L. Rogitz

(57) ABSTRACT

A catheter has a hollow conduit through which working fluid from a heat exchange system flows. The conduit in turn is configured to extend along a longitudinal central axis in a continuously varying non-constant azimuthal orientation so that it defines a non-round enclosed passageway through which blood can flow to exchange heat through a wall of the conduit with the working fluid flowing within the conduit.

5 Claims, 4 Drawing Sheets

(56) References Cited

U.S. PATENT DOCUMENTS

| | | |
|---|---|---|
| 4,638,436 A | 1/1987 | Badger et al. |
| 4,653,987 A | 3/1987 | Tsuji et al. |
| 4,661,094 A | 4/1987 | Simpson |
| 4,665,391 A | 5/1987 | Spani |
| 4,672,962 A | 6/1987 | Hershenson |
| 4,754,752 A | 7/1988 | Ginsburg et al. |
| 4,787,388 A | 11/1988 | Hofmann |
| 4,813,855 A | 3/1989 | Leveen et al. |
| 4,849,196 A | 7/1989 | Yamada et al. |
| 4,852,567 A | 8/1989 | Sinofsky |
| 4,860,744 A | 8/1989 | Johnson et al. |
| 4,906,237 A | 3/1990 | Johansson et al. |
| 4,941,475 A | 7/1990 | Williams et al. |
| 5,092,841 A | 3/1992 | Spears |
| 5,103,360 A | 4/1992 | Maeda |
| 5,106,360 A | 4/1992 | Ishiwara et al. |
| 5,192,274 A | 3/1993 | Bierman |
| 5,195,965 A | 3/1993 | Shantha |
| 5,211,631 A | 5/1993 | Sheaff |
| 5,269,758 A | 12/1993 | Taheri |
| 5,281,215 A | 1/1994 | Milder |
| 5,304,214 A | 4/1994 | DeFord et al. |
| 5,342,301 A | 8/1994 | Saab |
| 5,344,436 A | 9/1994 | Fontenot et al. |
| 5,370,675 A | 12/1994 | Edwards et al. |
| 5,383,856 A | 1/1995 | Bersin |
| 5,403,281 A | 4/1995 | O'Neill et al. |
| 5,433,740 A | 7/1995 | Yamaguchi |
| 5,437,673 A | 8/1995 | Baust et al. |
| 5,458,639 A | 10/1995 | Tsukashima et al. |
| 5,486,207 A | 1/1996 | Mahawili |
| 5,486,208 A | 1/1996 | Ginsburg |
| 5,507,792 A | 4/1996 | Mason et al. |
| 5,531,714 A | 7/1996 | Dahn et al. |
| 5,531,776 A | 7/1996 | Ward et al. |
| 5,624,392 A | 4/1997 | Saab |
| 5,634,907 A | 6/1997 | Rani et al. |
| 5,676,670 A | 10/1997 | Kim |
| 5,701,905 A | 12/1997 | Esch |
| 5,709,564 A | 1/1998 | Yamada et al. |
| 5,709,654 A | 1/1998 | Klatz et al. |
| 5,716,386 A | 2/1998 | Ward et al. |
| 5,730,720 A | 3/1998 | Sites et al. |
| 5,733,319 A | 3/1998 | Neilson et al. |
| 5,737,782 A | 4/1998 | Matsuura et al. |
| 5,776,079 A | 7/1998 | Cope et al. |
| 5,788,647 A | 8/1998 | Eggers |
| 5,837,003 A | 11/1998 | Ginsburg |
| 5,862,675 A | 1/1999 | Scaringe et al. |
| 5,895,418 A | 4/1999 | Saringer |
| 5,908,407 A | 6/1999 | Frazee et al. |
| 5,957,963 A | 9/1999 | Dobak, III |
| 5,980,561 A | 11/1999 | Kolen et al. |
| 6,019,783 A | 2/2000 | Philips et al. |
| 6,042,559 A | 3/2000 | Dobak, III |
| 6,051,019 A | 4/2000 | Dobak, III |
| 6,059,825 A | 5/2000 | Hobbs et al. |
| 6,096,068 A | 8/2000 | Dobak, III et al. |
| 6,110,139 A | 8/2000 | Loubser |
| 6,117,065 A | 9/2000 | Hastings et al. |
| 6,117,105 A | 9/2000 | Bresnaham et al. |
| 6,124,452 A | 9/2000 | Di Magno |
| 6,126,684 A | 10/2000 | Gobin et al. |
| 6,146,141 A | 11/2000 | Schumann |
| 6,146,411 A | 11/2000 | Noda et al. |
| 6,148,634 A | 11/2000 | Sherwood |
| 6,149,670 A | 11/2000 | Worthen et al. |
| 6,149,677 A | 11/2000 | Dobak, III |
| 6,231,594 B1 | 5/2001 | Dae |
| 6,261,312 B1 | 7/2001 | Dobak, III et al. |
| 6,283,940 B1 | 9/2001 | Mulholland |
| 6,287,326 B1 * | 9/2001 | Pecor .......................... 607/105 |
| 6,299,599 B1 | 10/2001 | Pham et al. |
| 6,338,727 B1 | 1/2002 | Noda et al. |
| 6,383,144 B1 | 5/2002 | Mooney et al. |
| 6,409,747 B1 * | 6/2002 | Gobin et al. ................... 607/113 |
| 6,416,533 B1 | 7/2002 | Gobin et al. |
| 6,428,563 B1 | 8/2002 | Keller |
| 6,450,990 B1 | 9/2002 | Walker et al. |
| 6,464,716 B1 | 10/2002 | Dobak, III et al. |
| 6,527,798 B2 | 3/2003 | Ginsburg et al. |
| 6,530,946 B1 | 3/2003 | Noda et al. |
| 6,544,282 B1 | 4/2003 | Dae et al. |
| 6,551,309 B1 | 4/2003 | Le Pivert |
| 6,554,791 B1 | 4/2003 | Cartledge et al. |
| 6,589,271 B1 | 7/2003 | Tzeng et al. |
| 6,605,106 B2 | 8/2003 | Schwartz |
| 6,610,083 B2 | 8/2003 | Keller et al. |
| 6,620,187 B2 | 9/2003 | Carson et al. |
| 6,620,188 B1 | 9/2003 | Ginsburg et al. |
| 6,624,679 B2 | 9/2003 | Tomaivolo et al. |
| 6,635,076 B1 | 10/2003 | Ginsburg |
| 6,635,079 B2 * | 10/2003 | Unsworth et al. ............ 623/1.11 |
| 6,679,906 B2 | 1/2004 | Hammack et al. |
| 6,685,733 B1 | 2/2004 | Dae et al. |
| 6,706,060 B2 | 3/2004 | Tzeng et al. |
| 6,716,188 B2 | 4/2004 | Noda et al. |
| 6,719,723 B2 | 4/2004 | Werneth |
| 6,719,779 B2 | 4/2004 | Daoud |
| 6,726,653 B2 | 4/2004 | Noda et al. |
| 6,740,109 B2 | 5/2004 | Dobak, III |
| 6,749,625 B2 * | 6/2004 | Pompa et al. .................. 607/105 |
| 6,799,342 B1 | 10/2004 | Jarmon |
| 6,843,800 B1 | 1/2005 | Dobak, III |
| 6,887,263 B2 | 5/2005 | Bleam et al. |
| 6,893,419 B2 | 5/2005 | Noda et al. |
| 6,969,399 B2 | 11/2005 | Schock et al. |
| 7,311,724 B1 * | 12/2007 | Ginsburg ....................... 607/105 |
| 7,510,569 B2 | 3/2009 | Dae et al. |
| 7,666,215 B2 | 2/2010 | Callister et al. |
| 7,822,485 B2 | 10/2010 | Collins |
| 7,846,193 B2 | 12/2010 | Dae et al. |
| 7,857,781 B2 | 12/2010 | Noda et al. |
| 8,105,262 B2 | 1/2012 | Noda et al. |
| 8,105,263 B2 | 1/2012 | Noda et al. |
| 8,105,264 B2 | 1/2012 | Noda et al. |
| 8,109,894 B2 | 2/2012 | Noda et al. |
| 2001/0007951 A1 * | 7/2001 | Dobak, III .................... 607/106 |
| 2001/0031946 A1 | 10/2001 | Walker et al. |
| 2001/0047196 A1 | 11/2001 | Ginsburg et al. |
| 2002/0013569 A1 | 1/2002 | Sterman et al. |
| 2002/0022823 A1 | 2/2002 | Luo et al. |
| 2002/0095198 A1 * | 7/2002 | Whitebook et al. ........... 607/100 |
| 2002/0103519 A1 * | 8/2002 | Dobak et al. .................. 607/105 |
| 2002/0128698 A1 * | 9/2002 | Dobak et al. .................. 607/105 |
| 2002/0145525 A1 | 10/2002 | Friedman et al. |
| 2002/0151942 A1 | 10/2002 | Walker et al. |
| 2002/0177846 A1 * | 11/2002 | Saab .............................. 604/45 |
| 2002/0183692 A1 | 12/2002 | Callister |
| 2002/0198579 A1 | 12/2002 | Khanna |
| 2003/0236496 A1 | 12/2003 | Samson et al. |
| 2004/0044387 A1 | 3/2004 | Pompa et al. |
| 2004/0089058 A1 | 5/2004 | De Haan et al. |
| 2004/0102825 A1 | 5/2004 | Daoud |
| 2004/0210231 A1 | 10/2004 | Boucher et al. |
| 2005/0010272 A1 * | 1/2005 | Pham et al. ................... 607/105 |
| 2005/0010273 A1 * | 1/2005 | Walker et al. ................ 607/105 |
| 2005/0156744 A1 | 7/2005 | Pires |
| 2007/0007640 A1 | 1/2007 | Harnden et al. |
| 2007/0076401 A1 | 4/2007 | Carrez et al. |
| 2008/0149100 A1 * | 6/2008 | Van Holst et al. ...... 128/204.17 |
| 2010/0228192 A1 * | 9/2010 | O'Dea et al. .................. 604/104 |
| 2011/0270368 A1 | 11/2011 | Ginsburg et al. |

FOREIGN PATENT DOCUMENTS

| | | |
|---|---|---|
| GB | 1183185 | 2/1985 |
| GB | 2212262 | 7/1989 |
| GB | 2383828 | 7/2003 |
| JP | 09-215754 | 8/1997 |
| JP | 10-0127777 | 5/1998 |
| JP | 10-305103 | 11/1998 |
| WO | 9001682 | 2/1990 |
| WO | 9304727 | 3/1993 |

(56) References Cited

FOREIGN PATENT DOCUMENTS

| WO | 9400177 | 1/1994 |
| WO | 9401177 | 1/1994 |
| WO | 9725011 | 7/1997 |
| WO | 9824491 | 6/1998 |
| WO | 9840017 | 9/1998 |
| WO | 9966970 A | 12/1999 |
| WO | 0010494 | 3/2000 |
| WO | 0113809 | 3/2001 |
| WO | 0164146 | 9/2001 |
| WO | 0176517 | 10/2001 |
| WO | 0183001 | 11/2001 |

OTHER PUBLICATIONS

F.W. Behmann, E. Bontke, "Intravasale Kühlung", Pflügers Archie, Bd. 263, S. 145-165 (1956).

Wilhelm Behringer, Stephan Prueckner, Rainer Kenter, Samuel A. Tisherman, Ann Radovsky, Robert Clark, S. William Stezoski, Heremy Henchir, Edwin Klein, Peter Safar, "Rapid Hypothermic Aortic Flush Can Achieve Survival without Brain Damage after 30 Minutes Cardiac Arrest in Dogs", anesthesiology, V. 93, No. 6, Dec. 2000.

Dorraine Day Watts, Arthur Trask, Karen Soeken, Philip Predue, Sheilah Dols, Christopher Kaufman; "Hypothermic Coagulopathy in trauma: Effect of Varying levels of Hypothermia on Enzyme Speed, Platelet Function, and Fibrinolytic Activity". The Journal of Trauma: Injury, Infection, and Critical Care, Vo. 44, No. 5 (1998).

\* cited by examiner

INTRAVASCULAR HEAT EXCHANGE CATHETER WITH NON-ROUND COILED COOLANT PATH

FIELD OF THE INVENTION

The present application relates generally to patient temperature control systems.

BACKGROUND OF THE INVENTION

It has been discovered that the medical outcome for a patient suffering from severe brain trauma or from ischemia caused by stroke or heart attack or cardiac arrest is improved if the patient is cooled below normal body temperature (37° C.). Furthermore, it is also accepted that for such patients, it is important to prevent hyperthermia (fever) even if it is decided not to induce hypothermia. Moreover, in certain applications such as post-CABG surgery, skin graft surgery, and the like, it might be desirable to rewarm a hypothermic patient.

As recognized by the present application, the above-mentioned advantages in regulating temperature can be realized by cooling or heating the patient's entire body using a closed loop heat exchange catheter placed in the patient's venous system and circulating a working fluid such as saline through the catheter, heating or cooling the working fluid as appropriate in an external heat exchanger that is connected to the catheter. The following U.S. patents, all of which are incorporated herein by reference, disclose various intravascular catheters/systems/methods for such purposes: U.S. Pat. Nos. 6,881,551 and 6,585,692 (tri-lobe catheter), U.S. Pat. Nos. 6,551,349 and 6,554,797 (metal catheter with bellows), U.S. Pat. Nos. 6,749,625 and 6,796,995 (catheters with non-straight, non-helical heat exchange elements), U.S. Pat. Nos. 6,126,684, 6,299,599, 6,368,304, and 6,338,727 (catheters with multiple heat exchange balloons), U.S. Pat. Nos. 6,146,411, 6,019,783, 6,581,403, 7,287,398, and 5,837,003 (heat exchange systems for catheter), U.S. Pat. No. 7,857,781 (various heat exchange catheters).

SUMMARY OF THE INVENTION

Accordingly, a catheter has a proximal segment configured to receive and return working fluid to a heat exchange system through supply and return lumens, respectively. The catheter also has a distal segment communicating with the proximal segment and configured to circulate working fluid therewith. The distal segment defines a supply conduit and a return conduit, with at least one of the conduits configured for conveying all fluid flowing therethrough along a non-round coiled path.

If desired, the supply conduit may be configured for conveying all fluid flowing therethrough along a non-round coiled path. In addition or alternatively, the return conduit can be configured for conveying all fluid flowing therethrough along a non-round coiled path.

In one example, the non-round path defines a rectangle when viewed in transverse. In another example, the non-round path defines a triangle when viewed in transverse. In either case, the non-round path can be established by intravascular balloon material or by flexible metal and can extend continuously along a longitudinal axis albeit with varying angles of extension.

In another aspect, a catheter includes a hollow conduit through which working fluid from a heat exchange system can flow. The conduit is configured to extend along a longitudinal central axis in a continuously varying non-constant azimuthal orientation so that it defines a non-round enclosed passageway through which blood can flow to exchange heat through a wall of the conduit with the working fluid flowing within the conduit.

In another aspect, a catheter includes a hollow heat exchange region through which working fluid can flow to exchange heat with blood flowing past the heat exchange region. The heat exchange region defines an elongated conduit extending along an axial axis of the catheter to define a central blood passageway bordered by the conduit, and blood can flow through the blood passageway when the catheter is positioned in a patient's blood vessel. Tangent lines at various points on the conduit do not establish a constant angle relative to a longitudinal axis defined by the conduit.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
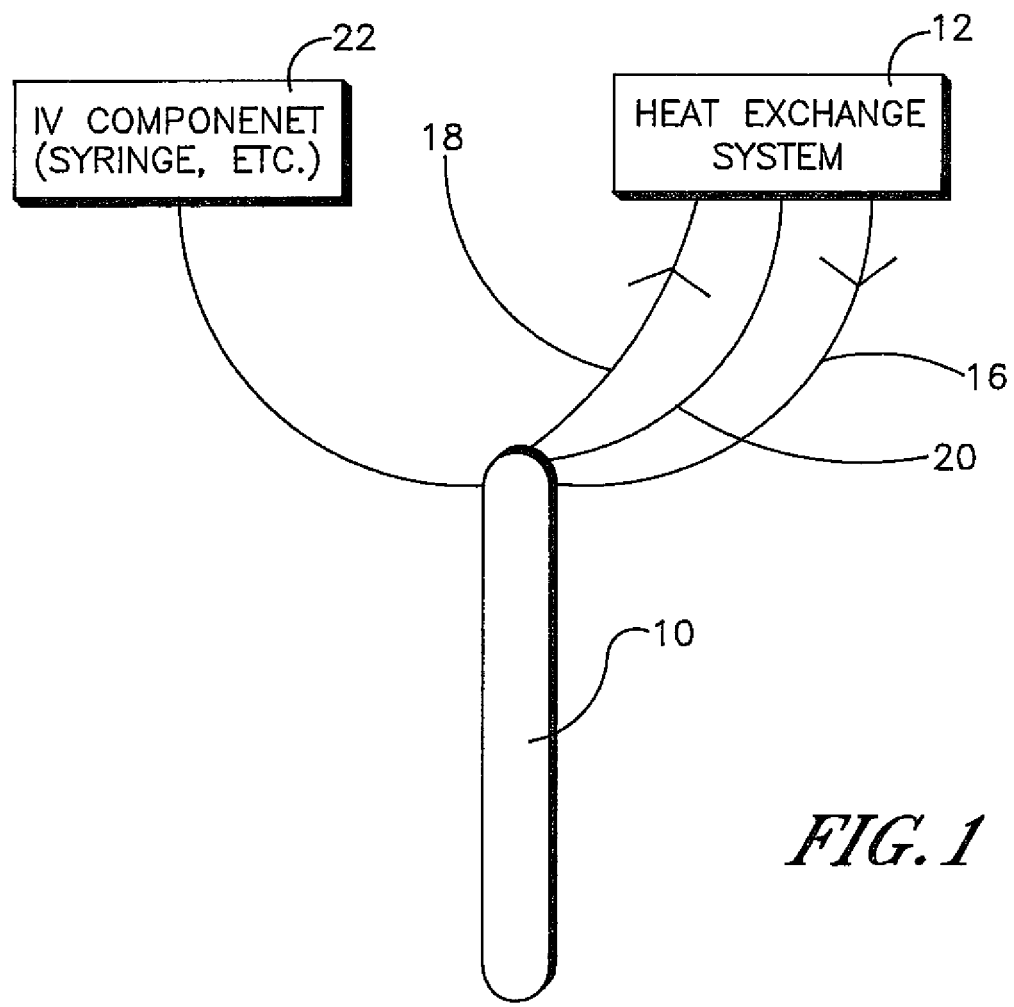
FIG. 1 is a schematic diagram showing an example catheter engaged with an example heat exchange system.

Referring initially to FIG. 1, an intravascular temperature management catheter 10 is in fluid communication with a catheter temperature control system 12 that includes a processor executing logic that in some non-limiting examples is in accordance with disclosure in the above-referenced system patents to control the temperature of working fluid circulating through the catheter 10 in accordance with a treatment paradigm responsive to patient core temperature feedback signals. In accordance with present principles, the catheter 10 can be used to induce therapeutic hypothermia in a patient 14 using the catheter, in which coolant such as but not limited to saline circulates in a closed loop, such that no coolant enters the body. Such treatment may be indicated for stroke, cardiac arrest (post-resuscitation), acute myocardial infarction, spinal injury, and traumatic brain injury. The catheter 10 can also be used to warm a patient, e.g., after bypass surgery or burn treatment, and to combat hyperthermia in, e.g., patient suffering from sub-arachnoid hemorrhage or intracerebral hemorrhage.

As shown, working fluid such a refrigerant may be circulated between the heat exchange system 12 and catheter 10 through supply and return lines 16, 18 that connect to the proximal end of the catheter 10 as shown. Note that as used herein, "proximal" and "distal" in reference to the catheter are relative to the system 12. A patient temperature signal from a catheter-borne temperature sensor may be provided to the system 12 through an electrical line 20 or wirelessly if desired. Alternatively, a patient temperature signal may be provided to the system 12 from a separate esophageal probe or rectal probe or tympanic sensor or bladder probe or other temperature probe that measures the temperature of the patient 14.

The catheter 10, in addition to interior supply and return lumens through which the working fluid is circulated, may also have one or more infusion lumens connectable to an IV component 22 such as a syringe or IV bag for infusing medicaments into the patient, or an instrument such as an oxygen or pressure monitor for monitoring patient parameters, etc.

The catheter 10 can be positioned typically in the vasculature of the patient 14 and more preferably in the venous system of the patient 14 such as in the inferior vena cava through a groin insertion point or the superior vena cava through a neck (jugular or subclavian) insertion point.

Figure 2:
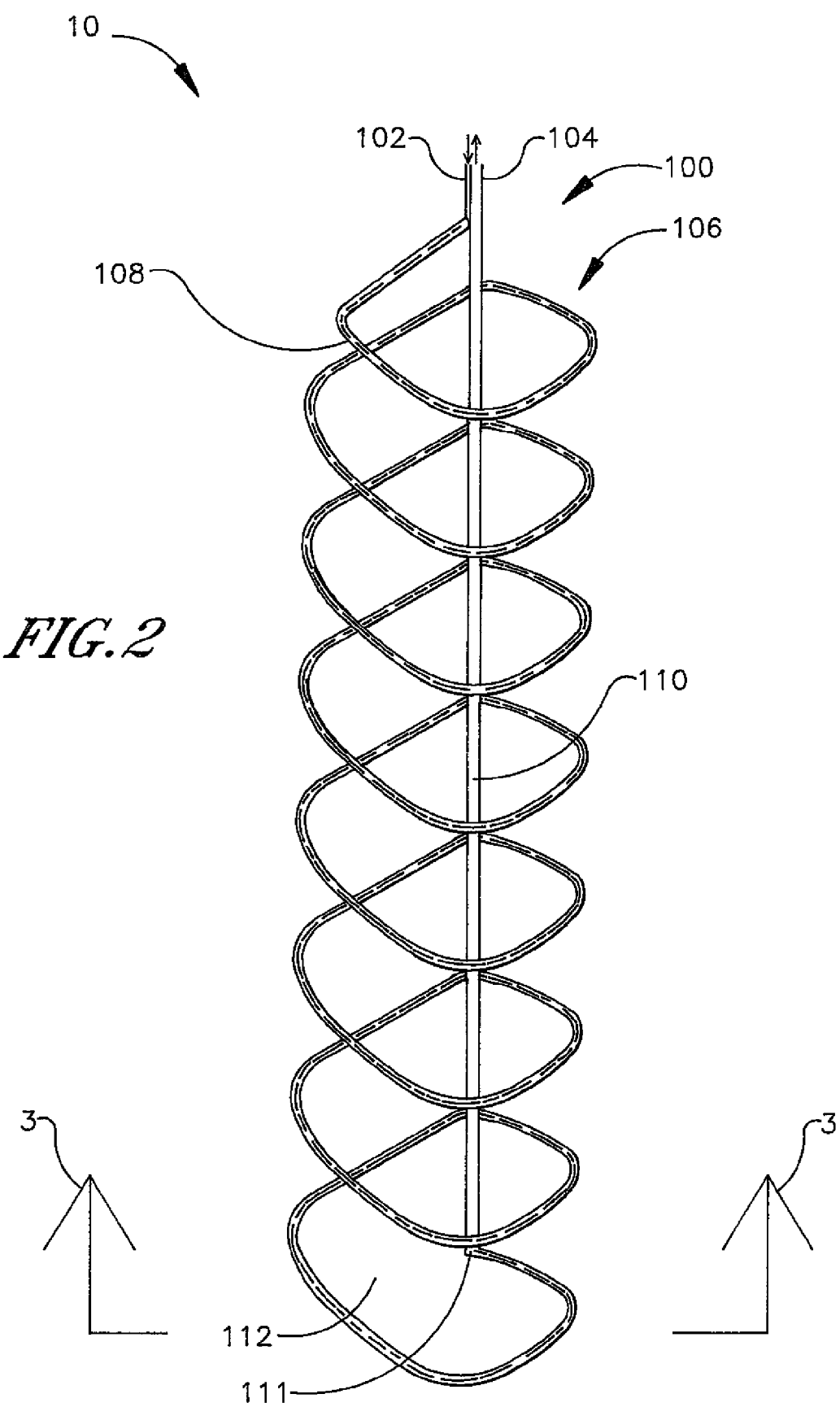
FIG. 2 shows an example heat exchange region which when viewed transversely appears to be rectangular.

Referring to FIG. 2, the present catheter 10 has a proximal segment 100 configured to receive working fluid from and return working fluid to the heat exchange system 12 through supply and return lumens, 102, 104, respectively. Connected in fluid communication with the proximal segment 100 is a distal segment 106 configured to circulate working fluid to and from the proximal segment (and, hence, the heat exchange system 12). As shown in FIG. 2, the distal segment 106 when inflated with working fluid defines a supply conduit 108 and a return conduit 110, and in the example shown in FIG. 2 the supply conduit 108 is configured for conveying all fluid flowing therethrough along a non-round coiled path, it being understood that the roles of the conduits may be reversed. The supply and return conduits 108, 110 join each other at a distal junction 111.

Figure 3:
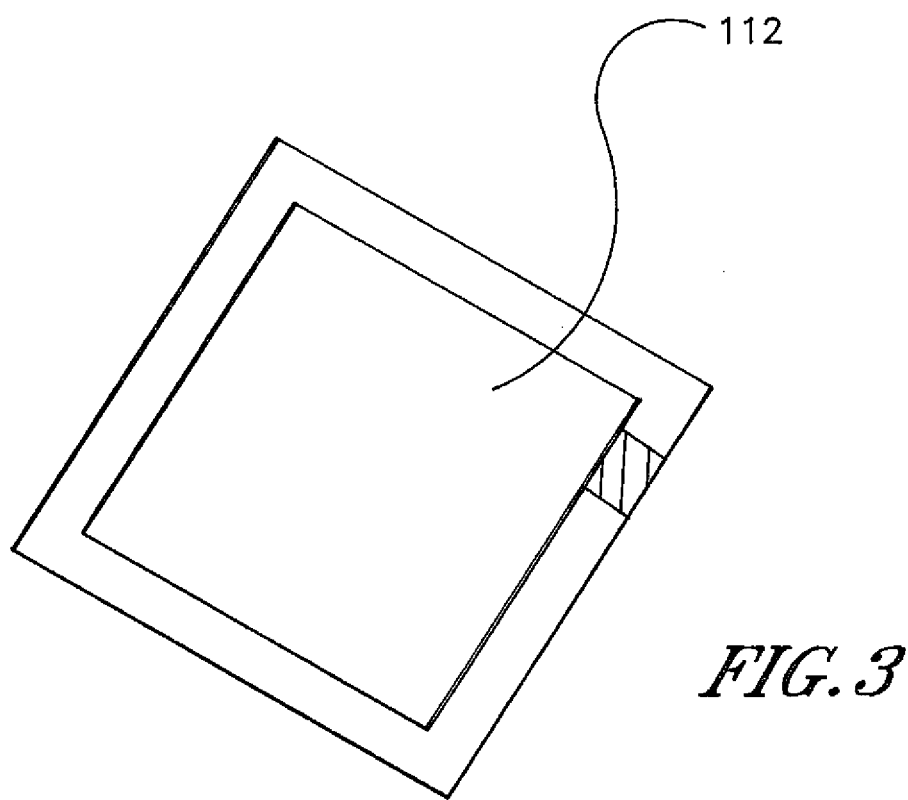
FIG. 3 is a cross-section taken along the line 3-3 in FIG. 2 illustrating that the heat exchange region when viewed transversely appears to be rectangular, with only a portion of the region being cross-hatched since remaining portions extend proximally or distally away from the point of cross-section.
Figure 5:
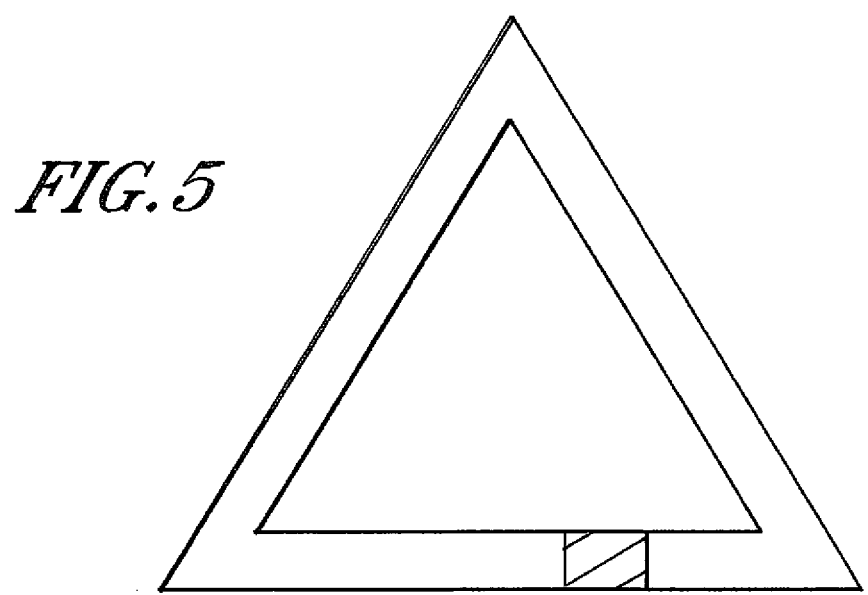
FIG. 5 is a cross-section taken along the line 5-5 in FIG. 4 illustrating that the heat exchange region when viewed transversely appears to be triangular, with only a portion of the region being cross-hatched since remaining portions extend proximally or distally away from the point of cross-section.
Figure 4:
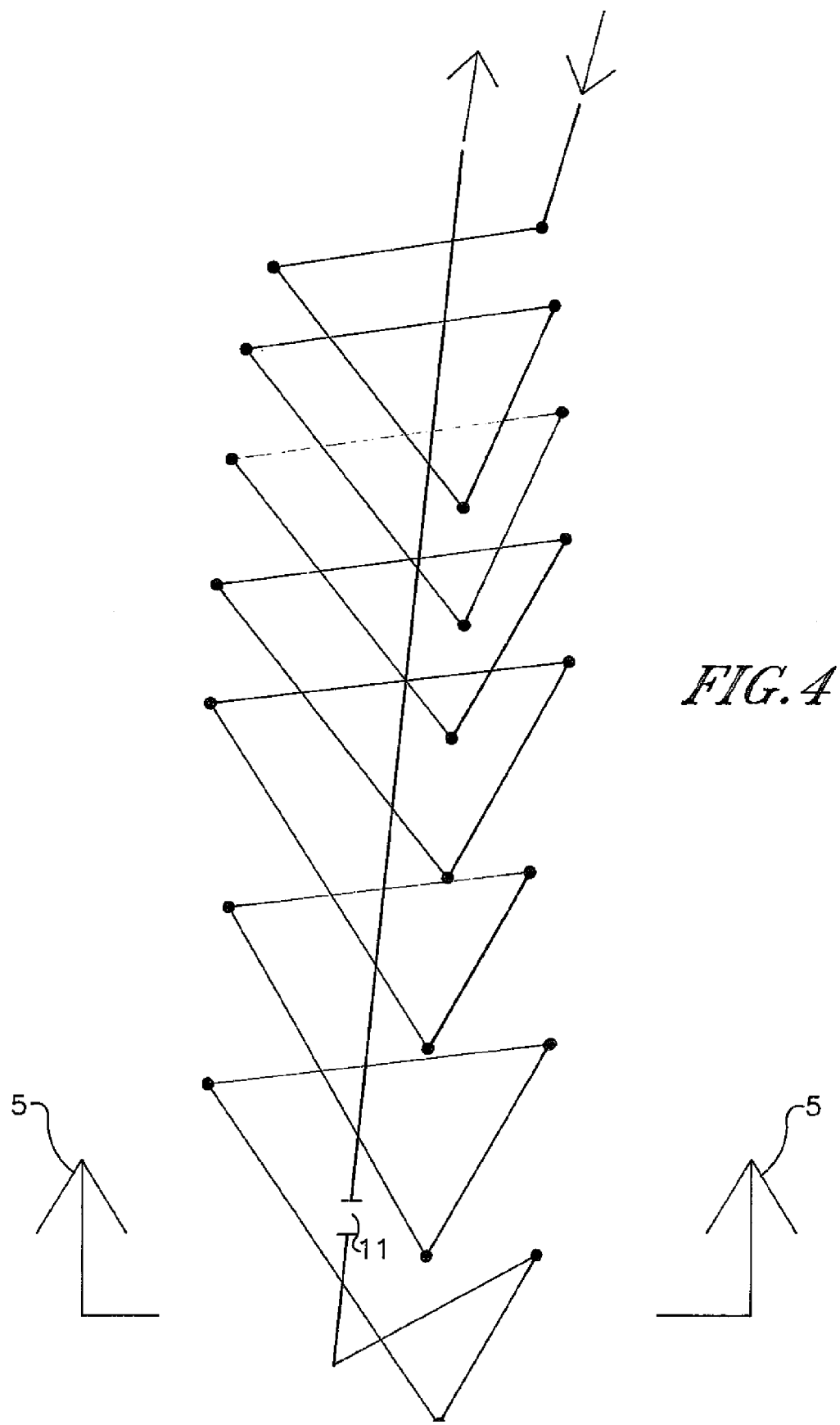
FIG. 4 shows a schematic diagram of another example heat exchange region which when viewed transversely appears to be triangular.

In the example of FIGS. 2 and 3, the non-round path of the supply conduit 108 defines a rectangle when viewed in transverse. In another example shown in FIGS. 4 and 5, the non-round path defines a triangle when viewed in transverse. In either case, the non-round path can be established by intravascular balloon material and can extend continuously along a longitudinal axis albeit with varying angles of extension.

Note that the tangent lines at various points on the conduit 108 do not establish a constant angle relative to the longitudinal axis defined by the conduit. In other words, the ratio of curvature of the conduit to torsion is not constant along the length of the conduit, but constantly varies along the length of the conduit.

Blood may flow through the non-round passageway 112 as well as around the periphery of the supply conduit 108 when the catheter 10 is advanced into a patient and working fluid from the heat exchange system 12 is circulated through the catheter 10. The blood exchanges heat through the wall of the catheter with the working fluid flowing in the non-round coiled path defined by the supply conduit 108.

While the particular INTRAVASCULAR HEAT EXCHANGE CATHETER WITH NON-ROUND COILED COOLANT PATH is herein shown and described in detail, it is to be understood that the subject matter which is encompassed by the present invention is limited only by the claims.

What is claimed is:

1. A catheter, comprising:
   a proximal segment configured to receive and return working fluid to a heat exchange system through supply and return lumens, respectively; and
   a distal segment communicating with the proximal segment and configured to circulate working fluid therewith, the distal segment defining a supply conduit and a return conduit joining each other at distal junction, at least a first one of the conduits configured for conveying all fluid flowing therethrough along a non-round coiled path and a second one of the conduits being straight, wherein the non-round path defines a triangle when viewed in transverse.

2. The catheter of claim 1, wherein the supply conduit is configured for conveying all fluid flowing therethrough along a non-round coiled path.

3. The catheter of claim 1, wherein the return conduit is configured for conveying all fluid flowing therethrough along a non-round coiled path.

4. The catheter of claim 1, wherein the non-round path is established by intravascular balloon material.

5. The catheter of claim 1, wherein the coiled path extends continuously along a longitudinal axis albeit with varying angles of extension.

* * * * *